United States Patent [19]

Berry

[11] Patent Number: 5,895,428

[45] Date of Patent: Apr. 20, 1999

[54] LOAD BEARING SPINAL JOINT IMPLANT

[76] Inventor: Don Berry, 18434 Collins St. Apartment No.4, Tarzana, Calif. 91356

[21] Appl. No.: 08/742,451

[22] Filed: Nov. 1, 1996

[51] Int. Cl.$^6$ ...................................................... A61F 2/44
[52] U.S. Cl. ............................... 623/17; 623/16; 623/18; 606/60; 606/61; 403/87; 403/119
[58] Field of Search ........................... 623/16, 17, 18; 606/60, 61, 62; 403/87, 110, 114, 115, 119, 150; 248/923

[56] References Cited

U.S. PATENT DOCUMENTS

| 4,349,921 | 9/1982 | Kuntz. |
| 4,401,112 | 8/1983 | Rezaian. |
| 4,714,469 | 12/1987 | Kenna. |
| 4,759,769 | 7/1988 | Hedman et al.. |
| 4,874,389 | 10/1989 | Downey. |
| 4,904,261 | 2/1990 | Dove et al.. |
| 4,932,975 | 6/1990 | Main et al.. |
| 4,936,848 | 6/1990 | Bagby. |
| 4,997,432 | 3/1991 | Keller. |
| 5,002,576 | 3/1991 | Fuhrmann et al.. |
| 5,047,055 | 9/1991 | Bao et al.. |
| 5,071,437 | 12/1991 | Steffe. |
| 5,145,134 | 9/1992 | Hashimoto ............................ 248/923 |
| 5,246,458 | 9/1993 | Graham ................................. 606/61 |
| 5,258,031 | 11/1993 | Anderson. |
| 5,306,307 | 4/1994 | Senter et al.. |
| 5,306,308 | 4/1994 | Gross et al.. |
| 5,306,309 | 4/1994 | Wagner et al.. |
| 5,401,269 | 3/1995 | Büttner-Janz ........................... 623/17 |
| 5,404,182 | 4/1995 | Nomura .................................. 248/923 |
| 5,425,773 | 6/1995 | Boyd et al.. |
| 5,458,638 | 10/1995 | Kuslich et al.. |
| 5,458,641 | 10/1995 | Jiminez. |
| 5,458,642 | 10/1995 | Beer et al.. |
| 5,474,555 | 12/1995 | Puno et al.. |
| 5,489,308 | 2/1996 | Kuslich et al.. |
| 5,507,816 | 4/1996 | Bullivant. |
| 5,534,029 | 7/1996 | Shima .................................... 623/17 |
| 5,538,427 | 7/1996 | Hoffman et al. ........................ 623/16 |
| 5,556,431 | 9/1996 | Büttner-Janz ........................... 623/17 |
| 5,588,625 | 12/1996 | Beak ...................................... 248/923 |
| 5,603,478 | 2/1997 | Wang ..................................... 248/923 |

FOREIGN PATENT DOCUMENTS

| 0317972 | 11/1988 | European Pat. Off. ................ 623/17 |
| 9404100 | 3/1994 | WIPO .................................... 623/17 |

Primary Examiner—Mark O. Polutta
Assistant Examiner—Tram Anh T. Nguyen
Attorney, Agent, or Firm—Curtis L. Harrington

[57] ABSTRACT

An implant is provided which has an upper member which pivots and is locked to a lower member and engages adjacent vertebrae and have surfaces which are ceramic and will allow bone growth into such surfaces and thus bonding with the adjacent vertebra. The opposing and bearing surfaces of the upper and lower member are coated with ceramic zirconium for long wear. Since the upper and lower members are captured, the implant device herein cannot be forced out of place by spinal tension. Particularly for the lower spinal vertebrae, the option of securing the upper and lower members with screws is facilitated. A vertebral replacement system using components in common with the implant is used to make a spaced connection between two pivoting points and is used to replace badly damaged vertebrae where the load bearing portion of the vertebra will be insufficient to allow normal support. It is expected that the implant and vertebral replacement will have several sizes corresponding to the spinal cross sectional shape being bonded to, and that exact dimensioning will be obtained through tomographic scans to enable rapid final sculpting of a highly customized implant.

13 Claims, 7 Drawing Sheets

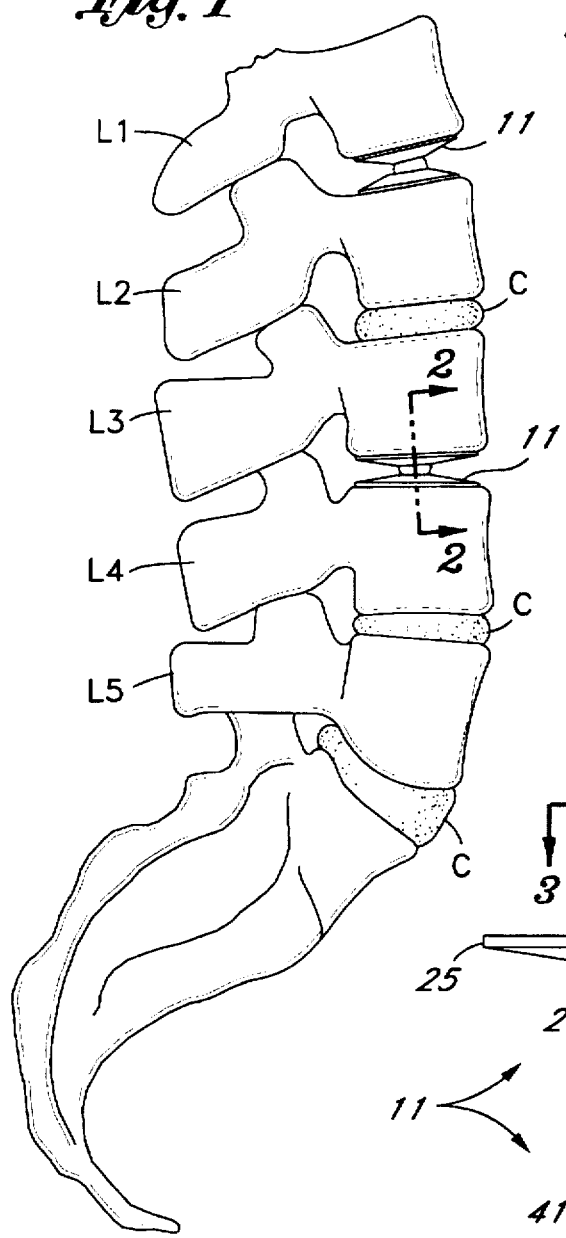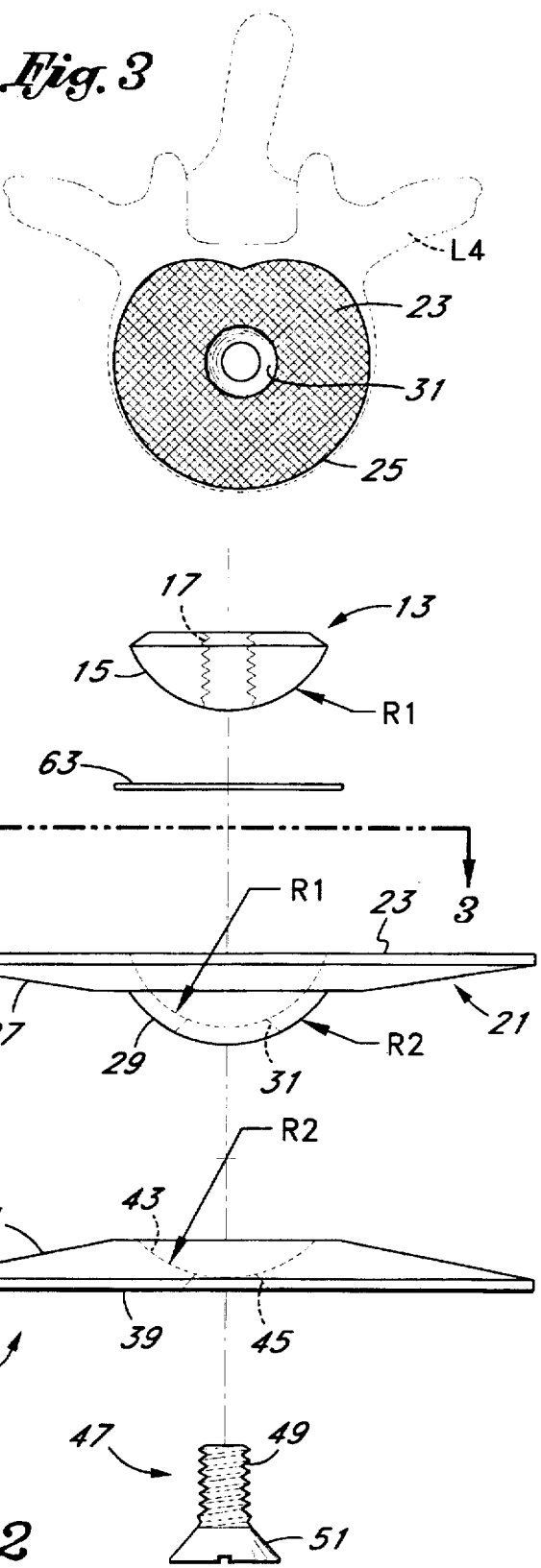

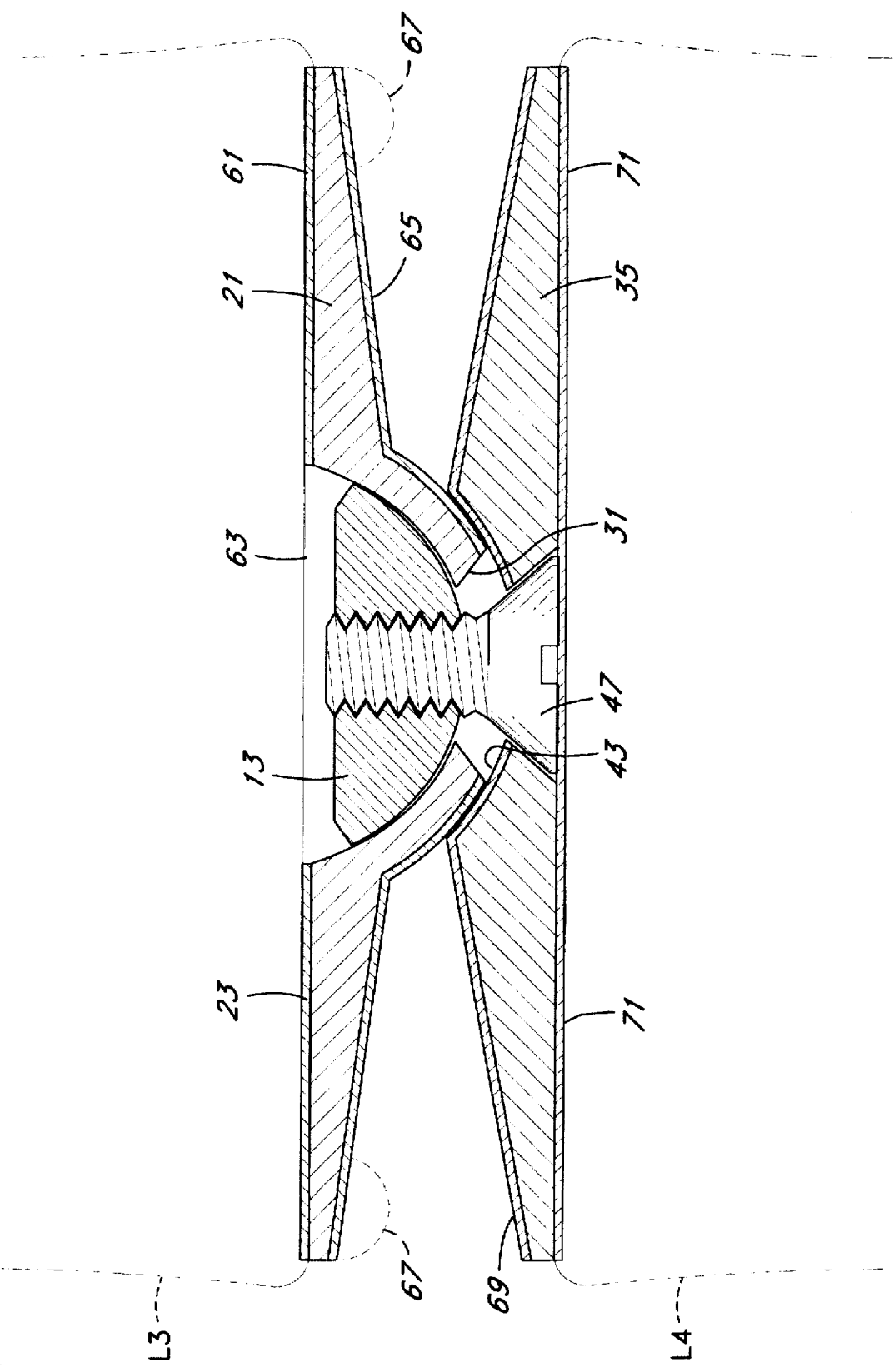

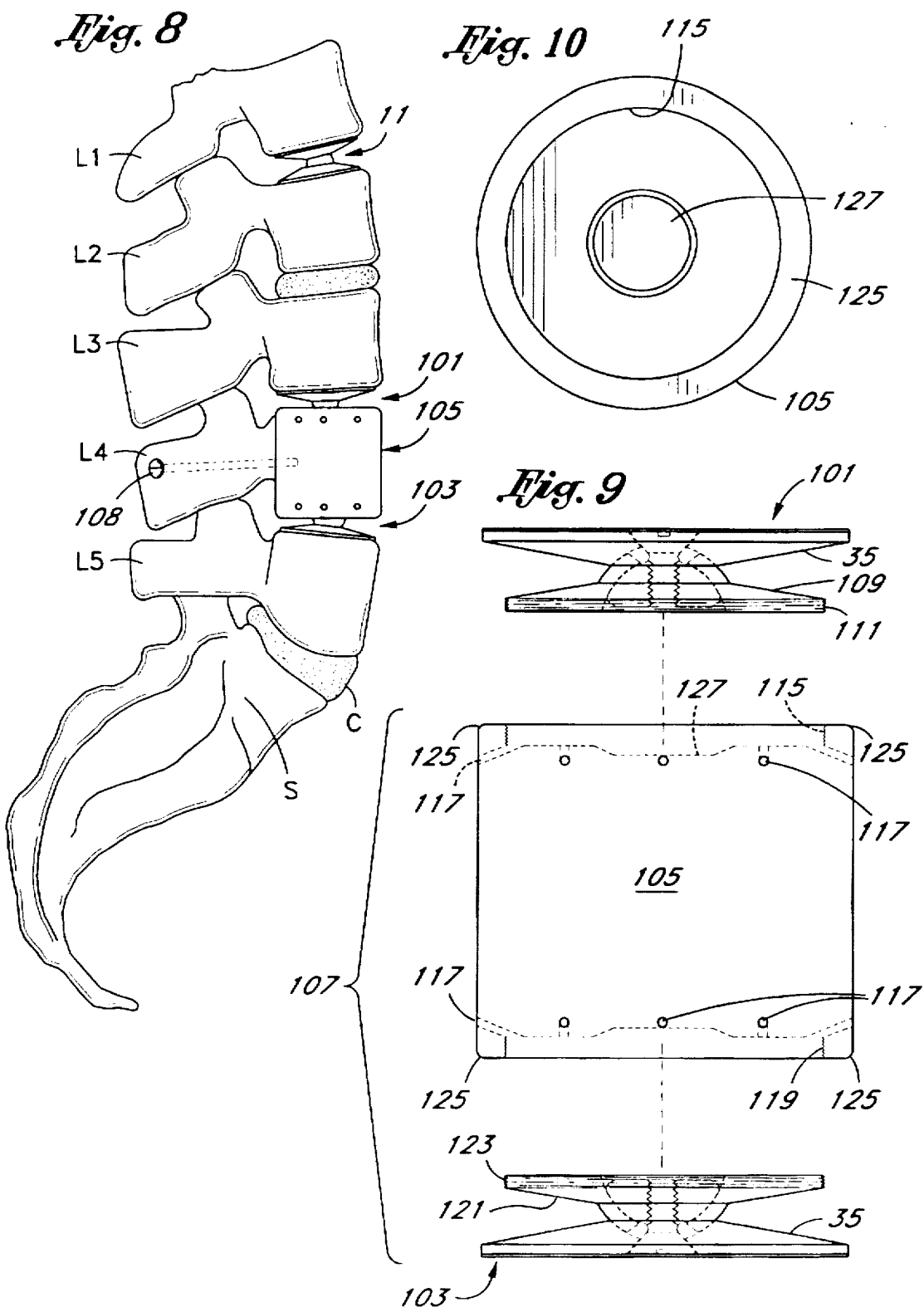

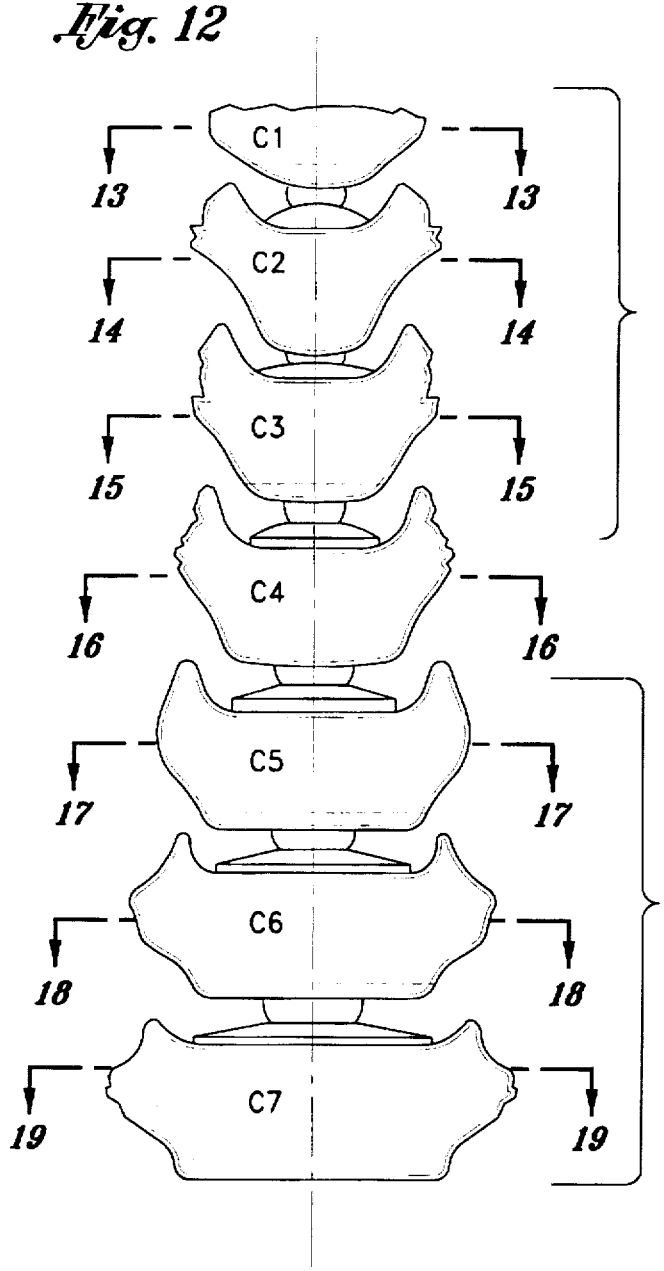

5,895,428

LOAD BEARING SPINAL JOINT IMPLANT

FIELD OF THE INVENTION

The present invention relates to a spinal joint implant which allows limited angular displacement in both the forward and side directions and which bonds to the vertebrae.

BACKGROUND OF THE INVENTION

Currently the main method used for spinal vertebra damage is the spine fusion. Fusion is an undesired method of dealing with the problem and can cause damage to adjacent vertebrae since it is the adjacent vertebra which must make up for the angular displacement lost due to the fusion of any two fused vertebrae.

The objective in any spine repair includes maintenance of safety to the spinal cord and its nerve roots and that of supporting the body and head in a variety of postures during normal movement of the arms, legs, and torso. Fusion will not enable the second objective to be fully realize. Coupled with the further damage which can occur in repairing vertebrae with fusion, fusion comes nowhere near accomplishing both objectives.

A wide variety of devices have been proposed for use in implantation into the spinal column. There are several main drawbacks for the devices currently in use. One of the most important shortcomings of the currently used implant devices involves their ability to separate when the spinal column is either placed under tension (as in doing pull ups or inversion therapy) or when loading is lessened. Under either of these conditions, one half of the load device could either be forced from its position in the spinal column, or at best the two load members could fail to re-mate. The result would be the necessity to either re-enter the patient for adjustment or an exterior attempt to get the load members to re-mate.

Other prostheses have attempted to imitate the intervertebral fribrocartilaginous discs. Bonding and support which imitates the human action of such discs is not realistically achievable. Again, since these soft discs can always slip out of their place, a disastrous breakdown of such a system is always possible.

It is clear that there is a severe need for a superior surgical joint replacement device; particularly, a replacement for a dislocated, ruptured or damaged vertebra due to spondylolysis. An estimated annual incidence of spinal cord injury (SCI), and its associate vertebrae injuries, is between 30 and 40 cases per million population in the U.S. Based on the 1992 census population of 254 million, these rates correspond to 7,600 and 10,000 new cases each year.

The number of people in these United States who are alive today and have SCI has been estimated to be between 721 and 906 per million population. This corresponds to between 183,000 and 203,000 persons. Spinal fusion is frequently used as a treatment for lower back pain and intervertebral disk degeneration, and the use of internal fixation has increased the ability of a surgeon to obtain a solid fusion. There is increased concern, however, that the biomechanical rigidity of the fusion and internal fixation may predispose adjacent spinal motion segments to rapid deterioration. Long-term follow up of patients undergoing a successful fusion indicates that 50 percent will continue to have complaints of back pain. As in other joints, alternatives to fusion of a spinal motion segment have inherent advantages.

Researchers have attempted to design a successful intervertebral disk arthroplasty device for years. For example, U.S. Pat. Nos. 4,946,378 & 4,874,389 discloses an artificial disk having a pair of end bodies with a medical synthetic polymeric intermediate member held between the end bodies. The intermediate member apparently provides some flexibility. Somewhat similarly, U.S. Pat. Nos. 4,932,975 & 5,002,576 discloses an artificial disk having end cover plates separated by a closed corrugated tube which is filled with a visco-elastic material, like a body-compatible silicone or elastomer. Other approaches are shown in U.S. Pat. Nos. 4,349,921, 4,714,469, 4,759,769, 4,863,476, 4,936,848, 4,997,432, 5,047,055, 5,071,437, 5,306,308, 4,349,921 and PCT patent WO 92/14423 discloses an artificial disk having convex superior and inferior surfaces corresponding to the adjacent vertebrae surfaces and being formed from two components to allow flexion and extension between the two components. U.S. Pat. No. 4,759,769 discloses and artificial disk having upper and lower members hinged together at the rear portion and biased apart at the front portion by stiff coil springs. U.S. Pat. No. 4,863,476 discloses a two portion spinal implant that is expandable so as to increase the spacing between the adjacent vertebrae. U.S. Pat. No. 4,936,848 shows an artificial disk having a spherical shape that is hollow and rigid. The sphere wall contains fenestration, open to the sphere cavity, for placing bone fragments therein. U.S. Pat. No. 4,997,432 shows an artificial disk having plates separated by a sliding core body normally consisting of a synthetic material. U.S. Pat. No. 5,047,055 discloses an artificial disk made of hydrogel material having a specified compressive strength and, when hydrated having the shape of a human disk. U.S. Pat. No. 5,071,437 shows an artificial disk having two rigid end-plates separated by, and connected to an elastomeric core material having flexure properties similar to those of a human disk. Finally, U.S. Pat. Nos. 4,595,663, 5,037,438, 5,425,773 and Re. 32,449 discloses the use of ceramic material, including Zirconia, for applications such a joint replacement. There are certain basic criteria a successful intervertebral disk arthroplasty device must fulfill.

Fatigue strength of the materials used in any joint replacement is of utmost importance. Since the average age of patients undergoing fusion is 36 years old, the life span of the device should exceed 51 years. Assuming the average patient walks 2 miles per day, with a stride of 2 feet=5,280 strides per day * 365 days=1,927,200 strides per year * 51 years=98,287,200 cycles+400,000 significant bends in the spine. A conservative estimate of the number of spinal loading cycles over 51 year period would be 98,687,200 cycles. To provide a safety factor, round off at 100 million cycles. A device for implant into the Human spine should be designed to have a fatigue limit of 100 million cycles. In addition to such durability, the material for a successful intervertebral disk arthroplasty device must be biocompatible. The wear of the implant must be kept to a minimum. Although the implant should be small enough to be contained within the anatomic confines of normal disk space, it is recognized that it may be advantageous to increase the prosthetic disk height in order to over distract the disk space to unload the joints posteriorly.

The present invention satisfies all these criteria.

SUMMARY OF THE INVENTION

An implant is provided which has an upper member which pivots and is locked to a lower member. The upper portion of the upper member and the lower portion of the lower member engage adjacent vertebra and have surfaces which are ceramic and will allow bone growth into such surfaces and thus bonding with the adjacent vertebra. The opposing and bearing surfaces of the upper and lower member are coated with ceramic zirconium for long wear. Because the upper and lower members are captured, the implant device herein cannot be forced out of place by spinal tension. As an additional precaution, and particularly for the lower spinal vertebra, the option of securing the upper and lower members with screws is facilitated. It is expected that the implant will have several sizes corresponding to the spinal cross sectional shape being bonded to, and it is also expected that exact dimensioning will be obtained through MRI scans and the like to enable rapid final sculpting of a highly customized implant.

BRIEF DESCRIPTION OF THE DRAWINGS

The invention, its configuration, construction, and operation will be best further described in the following detailed description, taken in conjunction with the accompanying drawings in which:

FIG. 1 is a side view of a lower spinal lumbar section and illustrating the placement of an implant according to the present invention;

FIG. 2 is an exploded plan view showing the components of the implant along its median line and taken with respect to line 2—2 of FIG. 1;

FIG. 3 is a view taken along line 3—3 of FIG. 2 and illustrating the outline of the upper surface 23 in relation to the portion of the vertebra upon which the implant rests;

FIG. 4 is an enlarged view of the implant of the present invention shown in section to illustrate both the porus ceramic coatings at the upper and lower surfaces, as well as the ceramic zirconium friction coating between the upper and lower members, as well an amorphous diamond coating between the spherical nut surfaces;

FIG. 8 is a side view of the lumbar region of the spine and illustrating the implant of FIGS. 1-7, and a pair of specialized implants and spacer to form a vertebral replacement assembly;

FIG. 9 is an exploded view of the vertebral replacement assembly and illustrating an upper implant fitting having a lower threaded fitting, a lower implant fitting having an upper threaded fitting, and a spacer fitting having an upper threaded bore and a lower threaded bore to permit joinder into an assembly, and drainage ports for both the upper and lower end of the spacer;

FIG. 10 is a downward view taken along line 10—10 of FIG. 9 looking onto the top of the spacer of the vertebral replacement assembly;

FIG. 12 illustrates the cervical vertebrae in a stacked arrangement to illustrate the positioning of the implant and to indicate in the later figures the approximate expected shapes of the support areas of those vertebra and the matching shape the upper and lower portions of the implant may assume;

FIGS. 13, 14, 15, 16, 17, 18, and 19 are downward views taken along lines 13—13, 14—14, 15—15, 16—16, 17—17, 18—18, and 19—19 and illustrate the shapes which the upper portion of the implant may assume.

DETAILED DESCRIPTION OF THE PREFERRED EMBODIMENT

Figure 5:
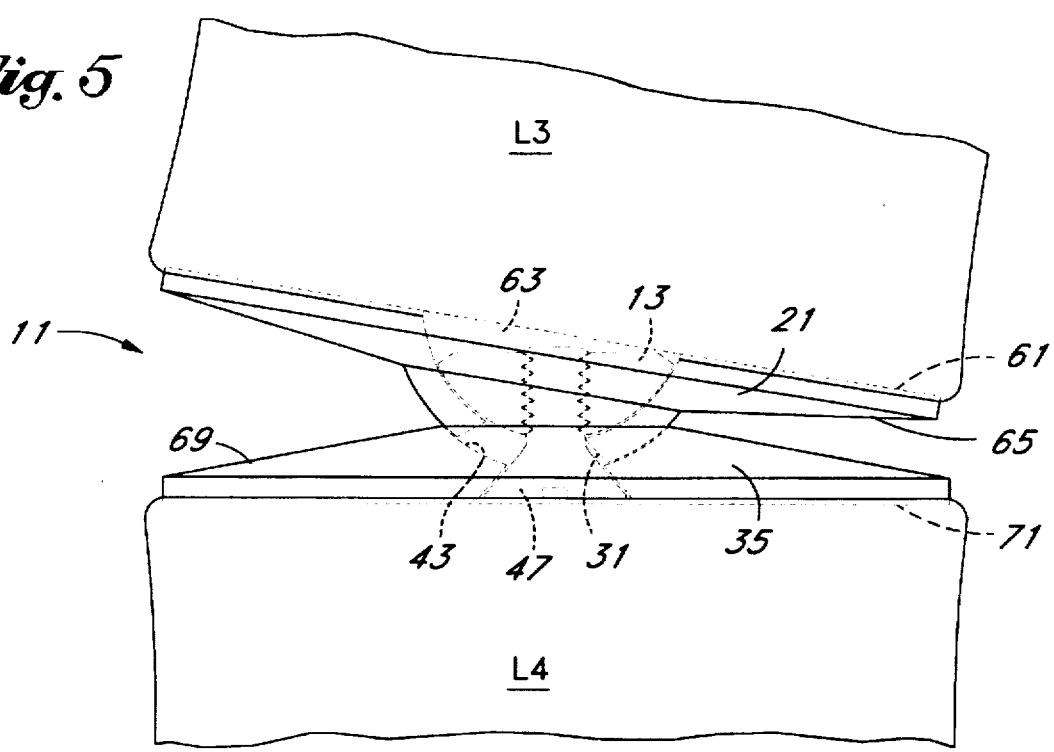
FIG. 5 is a view illustrating the implant angularly displaced to the left.

The description and operation of the invention will be best described with reference to FIG. 1. FIG. 1 illustrates, for example, the bottom of the spine which includes lumbar vertebrae L1, L2, L3, L4, and L5. Normally the intervertebral space of a healthy individual is occupied by an anulus fibrosus disc C. Where the vertebrae are damaged, there is no disc C to both hold the vertebrae together and to provide cushioning and angled movement. An implant 11 of the present invention is seen between the L1 and L2 vertebrae, as well as between the L3 and L4 vertebrae.

The implants 11 may exist in as many places along the spine as are necessary. As each vertebra L1, L2, L3, L4, and L5 for each individual is different, (as well as vertebra C1–C7, it is contemplated in the most preferred embodiment, where permissible, that the exact size of the implant 11 may be formed based upon a tomographic representation of each individual's vertebrae pair, between which the implant 11 is to be placed.

Referring to FIG. 2, an exploded view of an implant 11 having four components is taken along line 2—2 of FIG. 1. At the top of FIG. 2, a spherical nut 13 has a lower surface 15 which has an Ta-C amorphous diamond coating and has an external radius R1. The spherical nut 13 has an internally threaded bore 17. The spherical nut 13 may have upper surfaces to facilitate the grasping of the nut and the turning of the nut such that the internal threaded bore 17 securely engages a mating threaded screw.

Shown below the threaded nut 13 is an upper member 21. Upper member 21 has an upper metal surface 23 which may assume a roughened surface shape to enhance its ability to bond to an expand area or porus ceramic, which in turn will be utilized to bond to the bone tissue of the adjacent vertebra which it will abut when the insert 11 is in place. This roughened surface shape may include angular cross hatching to insure that the porus ceramic will be securely held in place.

The upper member 21 has an outer edge 25 and a transition toward its axial center that includes a conical surface 27 which transitions to a spherical section 29. The spherical section 29 has surface having a radius R2. At the center of the spherical section 29 is a conical opening 31 to admit a connecting member. The inside of the spherical section 29 has a radius R1 matching the radius R1 of the spherical nut 13.

Below the upper member 21 is a lower member 35. Lower member 35 has an outer rim 37 and a lower surface 39. From the outer rim 37, the surfaces opposing the upper member 21 include a conical surface 41, and a central radiused surface 43 having a radius R2 matching the radius R2 of the spherical section 29. At the center of the radiused surface 43 is an aperture 45 having a conical opening.

At the bottom of FIG. 2, a threaded screw 47 having a threaded outer surface 49 and conical surface 51 matching the conical opening of the aperture 45. As can be seen, the engagement of the conical surface 51 with the conical surface of the aperture 45 will cause the threaded screw 47 to be positionally fixed with respect to the lower member 35.

As can be seen the conically shaped aperture 45 will lock the threaded screw 47 into a fixed position with respect to the lower member 35. Since the spherical nut 13 will threadably engage the threaded outer surface 49 of the threaded screw 47, the spherical nut 13 will also be fixed with respect to the lower member 35. As such, the upper member 21 will be angularly displaced with respect to the other three components of the implant 11.

In particular, the motion will be limited by the contact of the upper member 21 and the lower member 35 at points near their outer edges 25 and 37 respectively, especially so long as the conical opening 31 is large enough to allow adequate angular displacement of the upper member 21 with respect to the lower member 35. The spacing and dimensions of the insert 11 are designed to enable proper angular displacement of the upper and lower members 21 and 35 and the vertebrae to which they are attached by the proper amount. The direct frictional surface contact will consist of the inner and outer surfaces of the spherical section 29 against the outer spherical surface of the spherical nut 13 and the central radiused surface 43 of the lower member 35, respectively.

Referring to FIG. 3, a view taken along line 3—3 of FIG. 2 illustrates the implant 11 in position with respect to the vertebra L4. As can be seen, in this view, the upper surface 23 reveals an outer edge 25 which has been trimmed or cut to fit the support area of the vertebra L4. The upper surface 23 is seen surrounding a surface 31 of the inside of the spherical section 29. Of course, the view of FIG. 3 does not include the spherical nut 13.

Referring to FIG. 4, a cross sectional view of fully assembled insert 11 is shown in order to illustrate the fine details, including the coatings on the insert 11 both to promote growth of the insert 11 to the bone tissue of the vertebra L3 and L4 shown in phantom, and coatings to minimize frictional wear between the frictional moving portions of the insert 11.

Beginning at the upper portion 21, which is made of titanium, the upper surface 23 of the upper member 21 is coated with a preferably porus, ceramic layer 61. Also shown at the upper portion of the upper member 21 is an optional cap 63. The cap 63 overlies the spherical nut 13. The cap 63 may have small apertures to allow drainage of any fluids which may collect within the space enclosed by the cap. Note that there is a significant space above the spherical nut 13 and the inside layer of the cap 63. This space exists to accommodate the outer edges of the spherical nut as the upper member 21 is tiltably displaced.

The bottom surfaces of the upper member 21 are coated with a layer of ceramic zirconium 65 over all lower surfaces evenly, including the conical surface 27 and the lower surface of the spherical section 29. Also shown as an option for the upper member 21 is a raised rim portion 67 shown in dashed line format. This structure can be placed completely or partially around the upper portion 21 in order to limit the angular displacement of the upper member 21 with respect to the lower member 35. This can be particularly useful where a longer axial length is provided for the insert to be implaced, but where the angular displacement is to be limited.

The upper side of the lower member 35, including conical surface 41 and central radiused surface 43, also has a coating of ceramic zirconium 69. Coated surface 69 will frictionally bear against coated surface 65. The lower surface 39 of the lower member 35 is coated with a preferably porus, ceramic layer 71. The layer 71 will bond and will enhance the growth of the bone tissue of the vertebra beneath the lower member 35 into the lower surface 39 of the lower member 35.

Note the threaded screw 47, which is preferably made of stainless steel (CRESS). It may be threadably engaged with the spherical nut 13 before the ceramic layer 71 is added, or an open area in the ceramic layer 71 may be provided to accommodate the insertion of the threaded screw 47. The addition of the ceramic layer 71 over the end of the threaded screw 47 is possible since the screw 47 will not move with respect to the lower member 35.

The lower member 35, which is preferably made of stainless steel and the upper member 21, which is preferably made of titanium 316 expanded metal, together will provide durability, resistance to corrosion and be of light weight. The spherical nut 13 and the threaded screw 47 are preferably made from CRES 316. Both the ceramic layers 61 and 71 may be preferably made from porus ceramic to promote and enhance the growth of bone tissue.

Referring to FIG. 5, the insert 11 is shown as rotating to the right. As can be seen, the spherical nut 13 does not rotate, but remains stationary with respect to the lower member 35. The clearance provided by extension of spherical nut 13 up to but short of the upper surface 23 enables the upper edges of the spherical nut 13 to refrain from bumping the upper inside surface of the cap 63.

Figure 6:
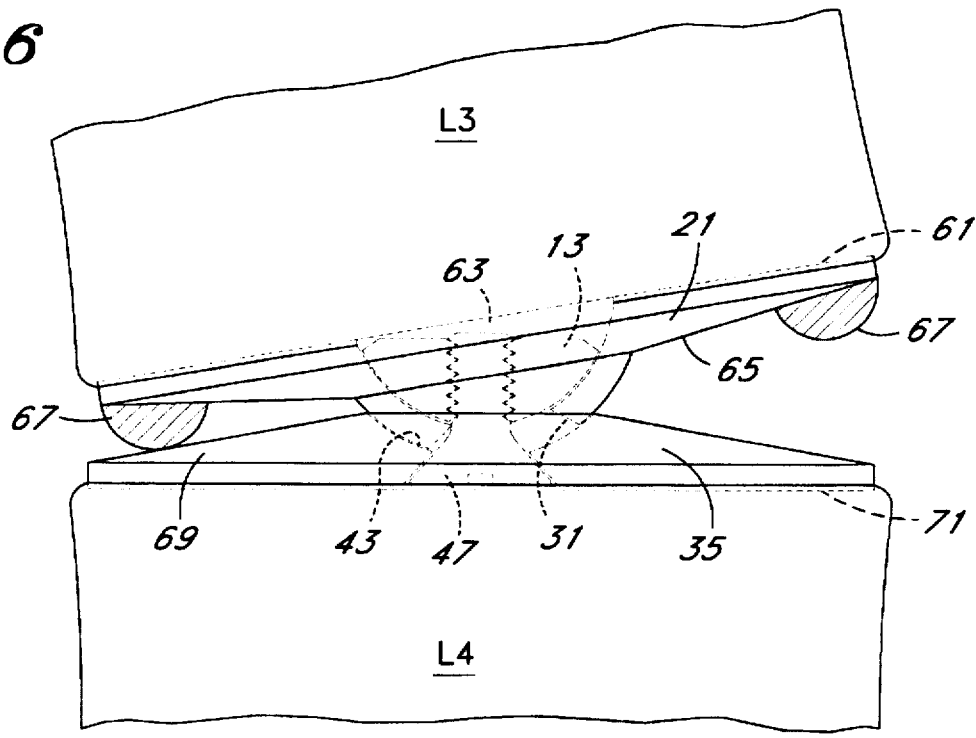
FIG. 6 is a view illustrating an implant with the raised rim portion contacting the upper portion of the implant.

Referring to FIG. 6, rotation of the implant 11 in the other direction is shown with respect to an implant 11 having the raised rim portion 67 on the upper member 21. As can be seen, the raised rim portion 67 contacts the lower member 35 and limits the angular motion of the upper member 21.

Figure 7:
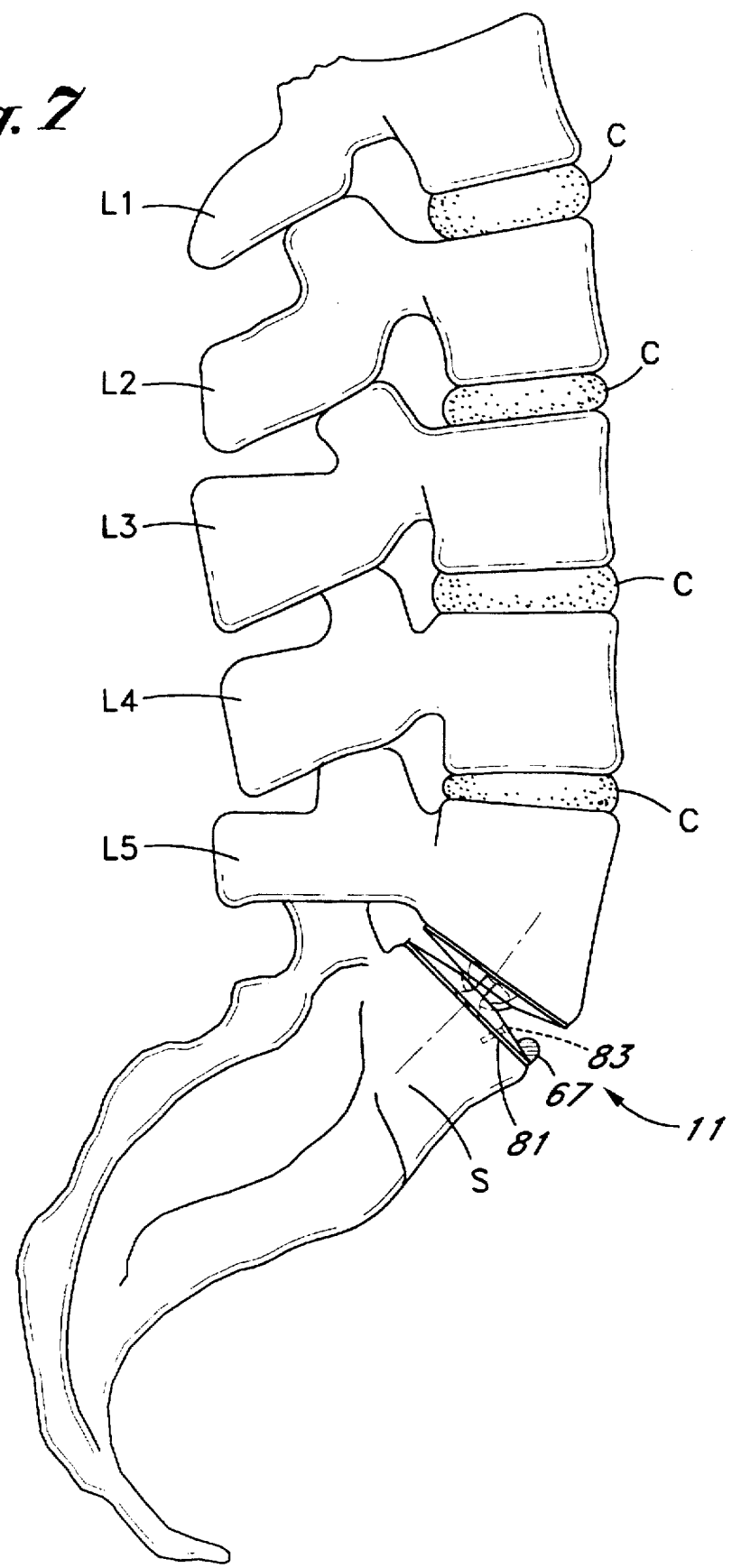
FIG. 7 is a side view of the lumbar region of the spine with an implant having a bore to permit a screw secured attachment to the vertebra, especially between the fifth lumbar vertebra and the sacrum.

One variation which is available as an option for the implant 11 is shown in FIG. 7 for an implant 11 in the lumbar area L5–L1 position, where spondylolysis & spondylolisthesis may be present. The disc "C" which previously occupied this space had a planar extent which was downwardly directed. In addition, the space occupied by the disc "C" is not evenly planar, but is instead wedge shaped. In this circumstance, the pressure on the implant 11 to become dislodged from between two vertebrae, or in this case from between the lumbar vertebra L5 and the sacrum "S" is greater than usual.

Here, the lower member 35 is fitted with an aperture 81 to facilitate the insertion of a retention screw 83. As can be seen, the raised rim portion 67 can provide some dimensional protection for the top of the retention screw 83. Of course, the bore 81 should be chamfered to accommodate the head of the screw 83 in assuming as low a profile as possible.

Referring to FIG. 8, a further aspect of the invention is seen. The implant 11 is useful where the disc "C" is damaged or degenerated, but the support portion of the vertebrae is sufficiently healthy and intact to enable the implant 11 to be introduced. As has been discussed, in some instances the support portion of the vertebra is so damaged that it must be removed. In the most damaged instances, it is partially dissolved and can be easily removed from the surrounding areas. Where it is clear that the vertebra cannot further support the weight of the spinal column, it must be carefully cut away while the spinous process from the vertebrae at the pedicle protects the spinal chord.

When this situation arises, a variation of the invention can be employed in the form of an upper implant fitting 101 having a lower threaded fitting, a lower implant fitting 103 having an upper threaded fitting, and a spacer fitting 105 having an upper threaded bore and a lower threaded bore. The combination of these three structures 101, 103, and 105 can be referred to as a vertebral replacement assembly 107. The assembly 107 has a pair of implants to more closely approximate the pivotal location of and spacing of a human vertebra and two intervertebral disc joints "C."

Also shown partially in dashed line format is one of a pair of optional elongate screws 108 which can extend through an extended portion of the vertebra L4 and into the fitting 105, in cases where further stabilization is needed.

Referring to FIG. 9, details of the interconnectability can be seen. The upper implant fitting 101 has a lower member 35 as was the case for implant 11. However, it is pivotally attached to a threaded fitting 109 having a threaded exterior 111 at its outer rim. This threaded exterior being 111 of expanded area has increased load bearing capability yet enabling a shallow depth of attachment. Although the term lower member 35 is used, it will become clear that the most stable of the upper member 21 and lower member 35 of the implant 11 is the lower member 35, and therefore the lower members 35 will be used as the outwardly disposed, bone engaging surfaces for the vertebra replacement assembly 107.

Except for the fact that the threaded fitting 109 carried an abbreviated diameter threaded exterior 111, the other components of the upper implant fitting 101 are the same as the components of the implant 11. Below the upper implant fitting 101 is the spacer 105 and showing an upper shallow threaded bore 115. Within the threaded bore 115 area, and carried within the spacer 105 are a series of drainage ports 117. These can help drain away any bodily fluids which work their way through the annular space between the threaded exterior 111 and the threaded bore 115, and are located at both ends of the spacer 105.

At the bottom of the spacer 105 is a lower shallow threaded bore 119, and structures similar to the drainage ports 117 are not believed to be needed.

The lower implant fitting 103 has a lower member 35 facing away from the assembly 107. However, it is pivotally attached to a threaded fitting 121 having a threaded exterior 123 at its outer rim. This threaded exterior being 123 of expanded area similarly has increased load bearing capability yet enabling a shallow depth of attachment, and will ideally match the threaded exterior 111. In some cases matching may be foregone to promote keying of the orientation of the spacer fitting 105 with regard to the upper and lower implant fittings 101 and 103.

Except for the fact that the threaded fitting 121 carried an abbreviated diameter threaded exterior 123, the other components of the lower implant fitting 103 are the same as the components of the implant 11, and it may be specifically identical to the upper implant fitting 103 where applicable. The threaded fitting 121 may also be fitted with drainage ports if there is any concern about fluids seeping or wicking into the threaded bore 119.

Note that where either the threaded surfaces 123 or 111 are threadably engaged into the threaded bores 115 or 119 that the rim 125 may dimensionally act in the same manner as the raised rim portion 67 shown in FIG. 2. It is equivalent because it extends continuously about the spacer 105. Thus, by controlling the depth to which the threaded fittings 109 and 121 enter the threaded bores 115 and 119, the rim 125 will be made to extend closer to the lower member 35 to restrict angular displacement or to extend less closer to the lower member 35 to enable a wider range of angular displacement.

Also at the center of the spacer 105 and within the upper shallow threaded bore 115, a depression 127 is seen. The depression 127 is provided as a structure to assist in draining away of fluid through one of the drainage channels 117. This is also seen in FIG. 10 as being concentrically located at the center of the spacer 105.

Figure 11:
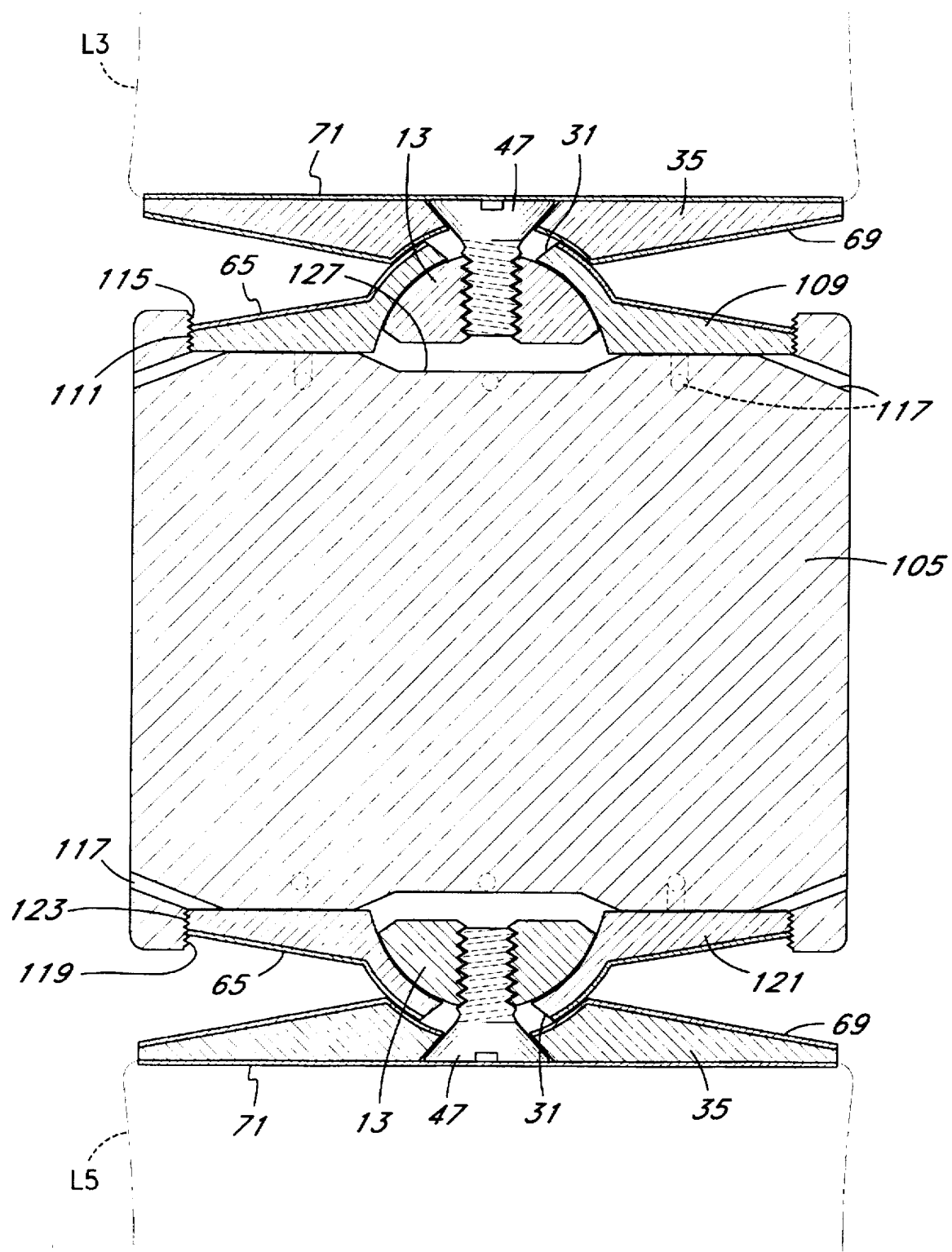
FIG. 11 is an enlarged sectional view of the vertebral replacement assembly shown in FIGS. 8-10.

The use of the rim 125 of the spacer 105 can be seen even more clearly by reference to FIG. 11 which is an expanded cross sectional view of the vertebra replacement assembly 107 of FIGS. 8–10. A lesser depth of the upper shallow threaded bore 115 or bore 119 can be achieved by forming with less depth or with the use of a shim located between the spacer fitting 105 and either of the threaded fittings 109 or 121.

Although FIG. 3 did illustrate the shape of one of the upper members 21, the other shapes have not been seen. Again, it is contemplated that the cervical, as well as lumbar vertebrae will benefit from the implant 11. Each of the upper and lower members 21 and 35 will have a customized shape matching the vertebra to which it is attached. Referring to FIGS. 12–19, it is expected that there will be average shapes, looking along the spine axially for each of the cervical vertebrae C1–C7, as well as a generalized shape for the lumbar vertebra L1–L5.

Although the diameter of each implant will be customized, it is expected that the overall diameters, as well as other dimensions to be discussed, will generally divide into three groups. Cervical vertebra C1–C3 form the first group, cervical vertebra C4–C7 will form the second group and lumbar vertebra L1–L5 will form the third group.

The other dimensions for each of the implants have been estimated to fall into three categories, to produce standard sizes for some of the structures of the inserts 11. For vertebrae C1–C3, the spherical nut should be formed to have a 0.031 inch clearance below the upper surface 23 of the upper member 21. The value of R1 is expected to be 0.157 inches, which will be the radius of the spherical surface 15 of the spherical nut 13, as well as the radius of the upwardly facing inner surface of the spherical section 29. The value of R2 is expected to be 0.188 inches which is the radius of the downwardly facing outer surface of the spherical section 29, as well as the radius of the upwardly facing central radiused surface 43.

The outer edge 25 will have an axial depth of about 0.016 inches, the axial height of the conical surface 27 is about 0.062 inches, and the height of the spherical section 29 over the conical surface 27 is about 0.079 inches. For the lower member 35, the axial length of the outer rim 37 is 0.016 inches and the height of the lower member 35 is about 0.125 inches. The overall diameter of both the upper and lower members 21 and 35 is expected to be about 0.625 inches in diameter.

For vertebrae C4–C7, the spherical nut should be formed to have a 0.047 inch clearance below the upper surface 23 of the upper member 21. The value of R1 is expected to be 0.187 inches, which will be the radius of the spherical surface 15 of the spherical nut 13, as well as the radius of the upwardly facing inner surface of the spherical section 29. The value of R2 is expected to be 0.219 inches which is the radius of the downwardly facing outer surface of the spherical section 29, as well as the radius of the upwardly facing central radiused surface 43.

The outer edge 25 will have an axial depth of about 0.016 inches, the axial height of the conical surface 27 is about 0.062 inches, and the height of the spherical section 29 over the conical surface 27 is about 0.079 inches. For the lower member 35, the axial length of the outer rim 37 is 0.016 inches and the height of the lower member 35 is about 0.125 inches. The overall diameter of both the upper and lower members 21 and 35 is expected to be about 1.250 inches in diameter.

For the lumbar vertebrae L1–L5, the spherical nut should be formed to have a 0.281 inch clearance below the upper surface 23 of the upper member 21. The value of R1 is expected to be 0.375 inches, which will be the radius of the spherical surface 15 of the spherical nut 13, as well as the radius of the upwardly facing inner surface of the spherical section 29. The value of R2 is expected to be 0.4375 inches which is the radius of the downwardly facing outer surface of the spherical section 29, as well as the radius of the upwardly facing central radiused surface 43.

The outer edge 25 will have an axial depth of about 0.031 inches, the axial height of the conical surface 27 is about 0.062 inches, and the height of the spherical section 29 over the conical surface 27 is about 0.064 inches. For the lower member 35, the axial length of the outer rim 37 is 0.031 inches and the height of the lower member 35 is about 0.125 inches. The overall diameter of both the upper and lower members 21 and 35 is expected to be about 1.750 inches in diameter.

For all of the inserts 11, the coating thicknesses are expected to be the same. The coatings of the preferably porus, ceramic layers 61 and 71 is about 0.031 inches in thickness, and the coating of the ceramic zirconium layers 65 and 69 is about 0.031 inches in thickness.

FIG. 12 illustrates the cervical vertebrae C1, C2, C3, C4, C5, C6 and C7 in a stacked arrangement to illustrate the positioning of the implant and to indicate in the later figures the approximate expected shapes of the support areas of those vertebrae and the approximate matching shape the upper and lower portions 21 and 35 of the implant which abut those vertebrae, may assume.

FIGS. 13, 14, 15, 16, 17, 18, and 19 are downward views taken along lines 13—13, 14—14, 15—15, 16—16, 17—17, 18—18, and 19—19 and illustrate the shapes of the upper and lower portions 21 and 35 of the implant.

The invention has been described with reference to a medically and surgically implantable joint which has surface treatment to encourage bonding to and growth with bone tissue, and while providing maximum life for the frictional contact between the moving parts thereof. The invention is sized to provide as little disruption to the adjacent vertebrae for the cartilage which the joint is being replaced as is possible.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A vertebral implant comprising:
   an upper member having a first side having a first planar surface and a first inner spherical surface, and a second side having a first conical surface and first outer spherical surface, said second side disposed oppositely with respect to said first side, said upper member having a central opening therethrough;
   a lower member having a third side facing said second side of said upper member, and having a second conical surface and a centrally located second inner spherical surface for interfitting with and bearing against said first outer spherical surface of said upper member, and having a fourth side having a second planar surface disposed oppositely with respect to said third side, said lower member having a central opening extending therethrough; and
   means, extending through said central opening of said upper and said lower members, for keeping said first outer spherical surface in close bearing and angular displacement relationship with said second inner spherical surface of said lower member.

2. The vertebral implant as recited in claim 1 wherein said first outer spherical surface of said upper member and said second inner spherical surface of said lower member are coated with a layer of ceramic zirconium for providing long frictional wear between said upper and said lower members.

3. The vertebral implant as recited in claim 1 wherein said first and said second planar surfaces are coated with a porus ceramic layer for promoting bonding with bone tissue.

4. The vertebral implant as recited in claim 1 wherein said first conical surface carries a raised rim portion to limit the angular displacement of said upper member with respect to said lower member.

5. The vertebral implant as recited in claim 1 wherein said means for keeping further comprises:
   a threaded member having a head and a threaded shaft extending through said central opening of said upper and lower members and fixed with respect to said lower member;
   a spherical nut having a threaded bore engaging said threaded shaft, said spherical nut having a second outer spherical surface for engaging said first inner spherical surface of said upper member, enabling said upper member to angularly pivot with respect to said lower member.

6. The vertebral implant as recited in claim 5 wherein said first and said second planar surfaces are coated with a porus ceramic layer for promoting bonding with bone tissue.

7. The vertebral implant as recited in claim 5 wherein said first outer spherical surface of said upper member and said second inner spherical surface of said lower member are coated with a layer of ceramic zirconium for providing long frictional wear between said upper and said lower members.

8. The vertebral implant as recited in claim 7 wherein said second outer spherical surface of said spherical nut is coated with a layer of tetrahedral amorphous diamond for providing long frictional wear between said spherical nut and said first inner spherical surface of said upper member.

9. The vertebral implant as recited in claim 8 wherein said first inner spherical surface of said upper member is coated with a layer of tetrahedral amorphous diamond for providing long frictional wear between said spherical nut and said first inner spherical surface of said upper member.

10. A vertebral replacement assembly comprising: an upper implant fitting including:
    a first threaded fitting having a first side having a first inner spherical surface, and a second side having a first conical surface and first outer spherical surface, said second side disposed oppositely with respect to said first side and defining a threaded exterior between said first and said second sides, said first threaded fitting having a central opening therethrough;
    a first lower member having a third side facing said second side of said first threaded fitting, and having a second conical surface and a centrally located second inner spherical surface for interfitting with and bearing against said first outer spherical surface of said first threaded fitting, and having a fourth side having a second planar surface disposed oppositely with respect to said third side, said first lower member having a central opening extending therethrough; and
    means, extending through said central opening of said first threaded fitting and said first lower member for keeping said first outer spherical surface of said first threaded fitting in close bearing and angular displacement relationship with said second inner spherical surface of said first lower member;

a spacer fitting having a first end having a first threaded bore engageable with said threaded exterior of said first threaded fitting, and a second end having a second threaded bore; and a lower implant fitting including:
 a second threaded fitting having a first side having a first inner spherical surface, and a second side having a first conical surface and first outer spherical surface, said second side disposed oppositely with respect to said first side and defining a threaded exterior between said first and said second sides for engagement with said second threaded bore of said second end of said spacer fitting, said second threaded fitting having a central opening therethrough;
 a second lower member having a third side facing said second side of said second threaded fitting, and having a second conical surface and a centrally located second inner spherical surface for interfitting with and bearing against said first outer spherical surface of said second threaded fitting, and having a fourth side having a second planar surface disposed oppositely with respect to said third side, said second lower member having a central opening extending therethrough; and means, extending through said central opening of said second threaded fitting and said second lower member, for keeping said first outer spherical surface of said second threaded fitting in close bearing and angular displacement relationship with said second inner spherical surface of said second lower member.

11. The vertebral replacement assembly as recited in claim 10 wherein said first outer spherical surfaces of said first and second threaded fittings and said second inner spherical surface of said first and second lower members are coated with a layer of ceramic zirconium for providing long frictional wear between said first and second lower members and said first and second threaded fittings.

12. The vertebral replacement assembly as recited in claim 10 wherein said second planar surfaces of said fourth sides of said first and second lower members are coated with a porus ceramic layer for promoting in growth with bone tissue.

13. The vertebral replacement assembly as recited in claim 10 wherein said spacer fitting has drainage ports leading from within said first threaded bore of said spacer fitting and through said spacer fitting to an outside surface of said spacer fitting.

* * * * *